(12) United States Patent
Meneses

(10) Patent No.: US 9,320,643 B2
(45) Date of Patent: Apr. 26, 2016

(54) APPARATUS AND METHODS FOR RELIEF OF ABDOMINAL DISCOMFORT

(76) Inventor: Nanette Meneses, Carlsbad, CA (US)

(*) Notice: Subject to any disclaimer, the term of this patent is extended or adjusted under 35 U.S.C. 154(b) by 889 days.

(21) Appl. No.: 13/371,286

(22) Filed: Feb. 10, 2012

(65) Prior Publication Data

US 2012/0209362 A1 Aug. 16, 2012

Related U.S. Application Data

(63) Continuation of application No. 11/895,898, filed on Aug. 27, 2007, now abandoned.

(60) Provisional application No. 60/840,874, filed on Aug. 28, 2006.

(51) Int. Cl.
| | | |
|---|---|---|
| A61F 7/02 | (2006.01) | |
| A61F 7/08 | (2006.01) | |
| A61F 7/00 | (2006.01) | |

(52) U.S. Cl.
CPC ........... *A61F 7/02* (2013.01); *A61F 2007/0001* (2013.01); *A61F 2007/0207* (2013.01)

(58) Field of Classification Search
CPC ................................................ A61F 2007/0207
See application file for complete search history.

(56) References Cited

U.S. PATENT DOCUMENTS

| | | | | |
|---|---|---|---|---|
| 1,739,989 A | * | 12/1929 | Sauter | 450/112 |
| 1,808,694 A | * | 6/1931 | Tognieri | 2/111 |
| 4,207,885 A | | 6/1980 | Hampton et al. | |
| 4,214,588 A | | 7/1980 | Byler | |
| 4,335,725 A | | 6/1982 | Geldmacher | |
| 4,580,547 A | | 4/1986 | Kapralis et al. | |
| 4,596,250 A | | 6/1986 | Beisang et al. | |
| 4,628,930 A | | 12/1986 | Williams | |
| 4,700,706 A | | 10/1987 | Munch | |
| 4,702,235 A | | 10/1987 | Hong | |
| 4,736,088 A | | 4/1988 | Bart | |
| 4,753,241 A | | 6/1988 | Brannigan et al. | |
| 4,756,311 A | | 7/1988 | Francis, Jr. | |
| 4,904,846 A | | 2/1990 | Oscadal | |
| 4,953,550 A | | 9/1990 | Dunshee | |
| 5,046,479 A | | 9/1991 | Usui | |
| 5,050,595 A | | 9/1991 | Krafft | |
| 5,050,596 A | | 9/1991 | Walasek et al. | |
| 5,050,598 A | | 9/1991 | Tucker | |
| 5,135,518 A | | 8/1992 | Vera | |
| 5,176,134 A | | 1/1993 | Hudson | |
| 5,184,613 A | | 2/1993 | Mintz | |
| 5,375,278 A | * | 12/1994 | VanWinkle et al. | 5/644 |
| 5,445,349 A | * | 8/1995 | Hart | A47B 21/0371 248/118 |
| 5,456,704 A | | 10/1995 | Kilcullen | |
| 5,476,492 A | | 12/1995 | Unrug | |
| 5,518,009 A | * | 5/1996 | Ruiz-Gonzalez | 128/869 |
| 5,584,086 A | * | 12/1996 | VanWinkle et al. | 5/644 |
| 5,948,010 A | * | 9/1999 | Adamec | 607/96 |

(Continued)

*Primary Examiner* — Kaitlyn Smith

(57) ABSTRACT

Therapy apparatus and method for use on, among others, human infants. In one embodiment, the apparatus provides apryrogenic enhancement of body heat production by external application of heated rubefacient herbs and seeds of the botanical family Crucifererae, in an elastic breathable and flexible fabric belt. Heating of the herbal belt in a microwave of other facility produces radiant heat, which when the apparatus is placed around the abdominal wall of an infant's body, provides therapy. A balance of enhanced body heat combined with the body's dissipation of heat creates a steady warming of the abdomen in conjunction with the relaxing olfactory effects of the herbal scents.

11 Claims, 3 Drawing Sheets

(56) References Cited

U.S. PATENT DOCUMENTS

| | | |
|---|---|---|
| 6,070,585 A | 6/2000 | Fery |
| 6,576,004 B2 | 6/2003 | Johnston |
| 6,637,429 B2 * | 10/2003 | Mundrick et al. ........... 128/96.1 |
| 6,699,271 B2 | 3/2004 | Clayton |
| 7,041,123 B2 | 5/2006 | Stapf et al. |
| 7,107,639 B2 | 9/2006 | Taricani |
| 7,125,417 B2 | 10/2006 | Mizrahi |
| 2002/0042641 A1 | 4/2002 | Johnson |
| 2002/0198580 A1 * | 12/2002 | Clayton ........................ 607/109 |
| 2005/0101220 A1 * | 5/2005 | Jackson ........................ 446/369 |
| 2005/0278854 A1 | 12/2005 | Taricani |
| 2006/0198874 A1 * | 9/2006 | Stanley ........................ 424/443 |
| 2007/0102461 A1 * | 5/2007 | Carstens ........................ 224/222 |
| 2007/0225783 A1 | 9/2007 | Korby et al. |
| 2008/0039913 A1 * | 2/2008 | Mizrahi ........................ 607/114 |
| 2008/0108863 A1 | 5/2008 | Stephenson |
| 2008/0208298 A1 * | 8/2008 | Mizrahi ........................ 607/108 |
| 2010/0100019 A1 | 4/2010 | Chen et al. |
| 2010/0217363 A1 * | 8/2010 | Whitely ........................ 607/112 |
| 2010/0298915 A1 | 11/2010 | Whitely |
| 2011/0054576 A1 | 3/2011 | Robinson et al. |

\* cited by examiner

APPARATUS AND METHODS FOR RELIEF OF ABDOMINAL DISCOMFORT

PRIORITY

This application is a continuation of and claims priority to co-owned and co-pending U.S. patent application Ser. No. 11/895,898 of the same title filed Aug. 27, 2007, which claims priority to U.S. Provisional Patent Application Ser. No. 60/840,874 filed Aug. 28, 2006 of the same title, each of which is incorporated herein by reference in its entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND OF THE INVENTION

1. Field of the Invention

The present invention relates to body therapy apparatus, and specifically in one aspect to external herbal warmers for abdominal muscle relaxation and aromatherapy for infants suffering from colic or fussiness.

2. Description of Related Technology

Several types of body warmers which use different principles of application and operation are evidenced in the prior art. Historically, body warming was achieved through water bottles, warm compresses, hot washcloths, steam, or herbal preparations of salves, creams, extracts and plasters. Such applications contained herbal extractions which caused a heating sensation when applied to the skin. These extractions, such as *Capsicum* (red pepper) or *Brassica* (mustard seed) also caused skin irritation or discomfort.

Recently, other methods of body warming developed popularity, including electrical heating pads, whereby an electrical current flows through a conductor of heat which is insulated and woven into a flexible cover or sheath. Patents using such methodology are evident when the heating pad is: (i) wrapped around the desired body part and fastened in place (U.S. Pat. No. 4,736,088 to Gordon Bart (1988); (ii) shaped as a garment to warm body parts (U.S. Pat. No. 5,050,595 to Krafft (breast warmer 1991) with battery power, and U.S. Pat. No. 4,628,930 to Williams for pelvic warming to abate menstrual cramping. (1986); (iii) shaped as a cushion for seating (U.S. Pat. No. 4,335,725 to Geldmacher 1982); and (iv) heated gel packs (U.S. Pat. No. 4,904,846 to Oscandal, 1990), each of the foregoing incorporated herein by reference in its entirety.

Other non-electric heating pads are evidenced in the prior art. Some use moisture for effect. Typically, the fabric is moistened with hot water, or heated in a microwave, then applied to the desired part of the body, and fastened or held in place. The warming effect only lasts until the heat stored in the moist pad is dissipated. See, e.g., U.S. Pat. No. 4,207,885 to Hampton et al. (1980); U.S. Pat. No. 4,753,241 to Brannigan et al. (1988); and U.S. Pat. No. 5,135,518 to Vera (1992), each of the foregoing incorporated herein by reference in its entirety.

Heating gels and fluid mediums are also used inside of pads. The fluids have a high heat capacity designed to reach specific temperatures when heated in a microwave. The products are then applied to the skin of the body to release heat until the gel or medium dissipates all the stored heat. See, e.g., U.S. Pat. No. 4,935,550 to Dunshee (1988); U.S. Pat. No. 4,756,311 to Francis Jr. (1988); and U.S. Pat. No. 4,700,706 to Munch (1987), each of the foregoing incorporated herein by reference in its entirety.

Some gel pads are designed for specific parts of the body. See, e.g., U.S. Pat. No. 5,050,598 to Tucker (1991) intended for use on the feet; shoe inserts described in U.S. Pat. No. 4,214,588 to Byler (1980). Hand warmers are disclosed in U.S. Pat. No. 5,050,596 to Walasek, et al. (1991), each of the foregoing incorporated herein by reference in its entirety.

Other pads contain chemical components that produce heat without the need for external heating. See, e.g., U.S. Pat. No. 5,176,134 to Hudson (1993); U.S. Pat. No. 4,580,547 to Kapralis et a. (1986); U.S. Pat. No. 4,596,250 Beisang, et al. (1986); and U.S. Pat. No. 5,046,479 to Usui (1991), each of the foregoing incorporated herein by reference in its entirety.

Despite the broad variety of body warming techniques and apparatus found in the prior art, all suffer from one or more significant disadvantages. Specifically, electric warmers most typically use house current (e.g., 115 VAC 60 Hz) from a wall plug. The user is dependent upon the proximity to a wall plug. Moreover, this method is not safely used while sleeping for overnight use. The unit can overheat and burn or injure the user, or the presence of moisture, exposed conductors, etc. may form an unwanted shorting and electrocution path. This method also offers no mobility, unless powered by an integrated battery or other energy storage system which can be bulky and awkward.

Gel and fluid heaters are also sometimes inconvenient to use. Heating action is not always even or uniform. Gel packs or fluid containers can also rupture and leak.

Warmers that operate by retaining body heat contain no external heat source and as a result, they have limited effectiveness in terms of therapy.

Hence, what is needed is a safe, effective easy-to-use, easily applied, generally lightweight, flexible, washable, warming therapy apparatus.

Another significant unsatisfied need relates specifically to the treatment of colic-stricken or "fussy" infants. Colic is a common affliction for infants, and can cause significant discomfort or distress for both the infant and its parent(s) or caregiver(s). It can often last for a significant period of time, and result in significant ingestion of air (from long-term crying), thereby exacerbating any gastrointestinal difficulties the infant is already experiencing.

Additionally, since infants cannot effectively communicate verbally or using other means (aside from crying), the parent/caregiver is unsure what is afflicting the infant, and hence treatments for the wrong condition may be erroneously administered.

Moreover, several "aroma" therapy or similar prior art devices intended for use on adults may contain substances which are at very least ineffective for infants, and at worst irritating and even deleterious to the health and/or well being of the infant. For example, seemingly benign substances such as rosemary and cinnamon may be ineffective and in fact irritating to infants.

Accordingly, a therapy apparatus and method specifically targeted at colic-stricken or fussy infants is also needed.

SUMMARY OF THE INVENTION

The present invention addresses the foregoing needs by disclosing therapy apparatus and methods useful for, inter alia, the treatment of colic-stricken or fussy infants.

In a first aspect of the invention, a therapy apparatus is disclosed. In one embodiment, the apparatus comprises a generally belt-like structure having a removable therapy medium and adapted to be worn around the mid-section of the subject (e.g., infant). The medium comprises a plurality of therapy ingredients adapted to both provide a warming sensation to the frontal mid-section, and optionally provide aroma therapy to the infant. The apparatus may be applied directly to the skin surface, or over (through) interposed clothing. One variant of the invention purposely avoids use of substances that may be irritating to the infant; e.g., rosemary and cinnamon.

In a second aspect of the invention, a method of applying therapy is disclosed. In one embodiment, the method comprises apyrogenic enhancement of body heat production by application of an apparatus comprising herbs and seeds of rubefacient varieties selected from the Cruciferae class of botanical herbs heated and applied to the abdomen, whereby a balance of body heat enhancement and dissipation of heat maintains a body warming effect at a substantially steady level.

In a second embodiment, the method comprises apyrogenic enhancement of body heat production by application of apparatus containing herbs and seeds of rubefacient varieties selected from the Cruciferae class of botanical herbs heated and applied to the abdomen of a subject, whereby an aromatic discharge of fragrant herbal smells provide therapy to said subject.

In yet another embodiment, the method comprises apyrogenic enhancement of body heat production by application of apparatus containing a compartment or pouch for insertion of an internal heat source which when applied to the abdomen, body heat enhancement and dissipation of heat cooperate to keep the body warming effect at a substantially steady level.

In yet another embodiment, the method comprises applying one or more of (i) heat and (ii) aroma therapy by placing a heat and/or aroma therapy source at the midsection of the infant to relieve colic or fussiness.

In a third aspect of the invention, an apparatus for treating colic afflicting an infant is disclosed. In one embodiment, the apparatus includes at least a first portion, the first portion comprising an internal heat source and at least a second portion, the second portion comprising an adjustable fastening mechanism and a permeable material for permitting a two-way air flow. The first and second portions are removably adjoined to one another. The internal heat source comprises hard red wheat berries and flax seed.

In a fourth aspect of the invention, a method of treating colic in an infant is disclosed. In one embodiment, the method includes (i) heating a heat source, the heat source comprising hard red spring wheat berries, (ii) placing the heat source in proximity to an apparatus comprising botanical herbs, and (iii) affixing the apparatus comprising botanical herbs and the heat source to an abdomen of the infant via a belt apparatus having a pouch for removably receiving said heat source and said apparatus comprising said botanical herbs. The act of affixing the apparatus comprises in one variant affixing the botanical herbs and the heat source to the abdomen of the infant and thereby enabling the infant to be proximately exposed to a discharge of a fragrant herbal aroma.

In a fifth aspect of the invention, an apparatus for treating a condition afflicting an infant is disclosed. In one embodiment, the apparatus includes (i) a therapy apparatus comprising an internal heat source comprising red spring wheat and natural aroma therapy components, and (ii) a retaining apparatus at least partly comprising a permeable fabric and configured to dispose and retain the therapy apparatus proximate to a portion of the infant's anatomy, the retaining apparatus comprising an adjustable waistband, the therapy apparatus being removable from the retaining apparatus. In one variant, the treated condition comprises colic, and the anatomical portion comprises front central abdomen of the infant. The internal heat source is disposed proximate to the natural aroma therapy components; the proximity of the internal heat source to the natural aroma therapy components causes a combination of aromatherapy and heat therapy.

In a sixth aspect of the invention, an apparatus for treating a condition afflicting a living subject is disclosed. In one embodiment, the apparatus comprises at least a first portion and a second portion, the first and second portions configured to detachably adjoin to one another. The first portion comprises an internal heat source and natural components, the internal heat source comprising red spring wheat berries. The second portion comprises an adjustable fastening mechanism and a substantially permeable material for permitting two-way air flow.

These and other aspects of the invention shall become apparent when considered in light of the disclosure provided below.

In a third aspect, an apparatus for treating a condition afflicting a living subject is disclosed. The apparatus comprises: a therapy apparatus; a retaining apparatus at least partly comprising a substantially permeable fabric and configured to dispose and retain the therapy apparatus proximate to a portion of the subject's anatomy, the retaining apparatus comprising an adjustable waistband, the therapy apparatus being removable from the retaining apparatus; wherein the living subject comprises an infant, the condition comprises colic, and the portion comprises the front central abdomen of the infant.

In one embodiment, the apparatus further comprises an internal heat source disposed proximate to the natural components. In a variant, the internal heat source comprises whole grain rice.

In a fourth aspect, a method of apyrogenic enhancement of body heat production by application of an apparatus comprising herbs and seeds of rubefacient varieties selected from the Cruciferae class of botanical herbs heated and applied to the abdomen, whereby a balance of body heat enhancement and dissipation of heat maintains a body warming effect at a substantially steady level. In this aspect, the herbs and seeds are substantially contained in a permeable and removable pouch.

In an embodiment, the abdomen comprises the abdomen of an infant human. In a variant, the apparatus comprises an internal heat source disposed proximate to the natural components and adapted to generate heat. In another variant, the internal heat source comprises whole grain rice, and the generating heat comprises heating the rice in a microwave oven.

In a fifth aspect, a method of apyrogenic enhancement of body heat production is disclosed. In an embodiment the method comprises application of an apparatus containing herbs and seeds of rubefacient varieties selected from the Cruciferae class of botanical herbs heated and applied to the abdomen of a subject, whereby an aromatic discharge of fragrant herbal aroma provides therapy to the subject where the herbs and seeds are substantially contained in a permeable and removable pouch.

In an embodiment, the subject comprises an infant human. In a variant, the apparatus comprises an internal heat source disposed proximate to the natural components and adapted to generate heat. In another variant, the internal heat source comprises whole grain rice, and the generating heat comprises heating the rice in a microwave oven.

In a sixth aspect, a method of apyrogenic enhancement of body heat production by application of apparatus containing a removable compartment or pouch for insertion of an internal heat source which when applied to the abdomen, body heat enhancement and dissipation of heat cooperate to keep a body warming effect at a substantially steady level is disclosed.

DETAILED DESCRIPTION OF THE INVENTION

Reference is now made to the drawings wherein like numerals refer to like parts throughout.

It is noted that while the invention is described herein primarily in terms of apparatus and methods for therapy on a infant human subjects, the invention may also be embodied or adapted to other age ranges, and even other warm-blooded species. All such adaptations and alternate embodiments are readily implemented by those of ordinary skill in the relevant arts, and are considered to fall within the scope of the claims appended hereto.

Overview

The apparatus and method of the invention offer safe, reliable, and durable solutions for colic and fussiness in, inter alia, infants and babies. Certain embodiments of the invention contain no electrical units, coils, cords, or power sources, an contain no chemicals, fluids, or gels. They are easy to use, portable, and convenient.

The use of (whole) herb seeds and products as the active rubefacient agent in the exemplary embodiments sustains a low heat level which is effective for the purposes intended without the risk of injury associated with other devices. The herb agents are intended and selected to last through the expected period of colic symptoms. The optional aromatherapy features also enhance and facilitate the effective relaxation of muscles and tension associated with fussiness and colic.

Optional coloration and visual elements of the apparatus also are selected to make the use of the apparatus appealing or interesting for the subject (e.g., infant), thereby associating use of the apparatus with a positive experience.

Another variant of the invention comprises a microwaveable or chemical heat source of the type known in the art such as e.g., whole grained rice, gel-packs, chemical heat packs, etc., which warms the aforementioned active rubefacient agent(s) and causes enhanced therapy emission and cooperative warming effect.

Description of Exemplary Embodiments

Figure 1:
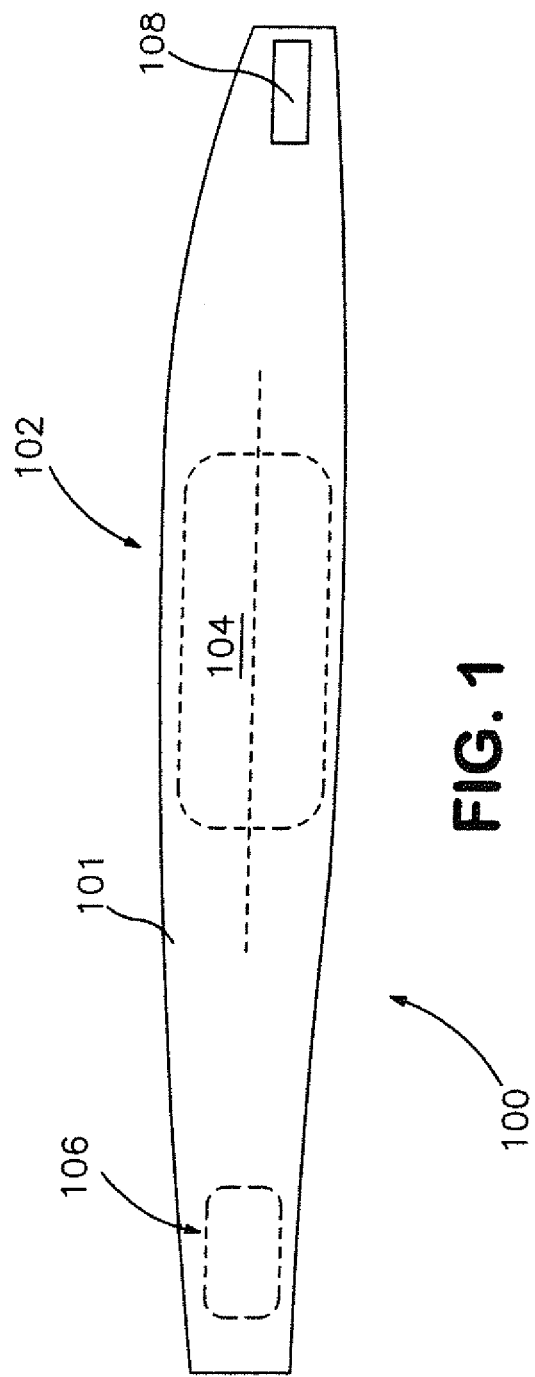
FIG. 1 is a front elevational view of one embodiment of the therapy apparatus of the invention.

Referring now to FIG. 1, one embodiment of the therapy apparatus of the invention is described in detail. As shown in FIG. 1, apparatus comprises a belt-like structure 101 having a waist band, or cummerbund made of cotton flannel or other cotton fabric which contains a pouch or compartment 102 for inclusion of one or more therapy elements 104 (FIGS. 2a-2c) comprising e.g., whole herbs, seeds, etc. as described in greater detail below, and/or an internal auxiliary heating source such as a heated gel pack (see gel and chemical patents previously incorporated herein, for exemplary types of devices that may be used with the invention). See also e.g., U.S. Pat. No. 7,041,123 to Stapf, et al. issued May 9, 2006 entitled "Warming pack with temperature uniformity and temperature stabilization", and U.S. Pat. No. 5,184,613 to Mintz issued Feb. 9, 1993 entitled "Thermal pack heel warming apparatus for a neonate or infant", each of the foregoing being incorporated herein by reference in its entirety.

It will be appreciated, however, that the therapy element 104 can conceivably be used alone (i.e., without the belt 101), or within other non-belt apparatus such as pads, clothing inserts, etc.

The illustrated belt 101 also comprises fastening apparatus 106, 108, such as a Velcro strip for fastening the belt around the abdomen. Elastics of the kind well known in the garment arts may also be used if desired.

The fabric selected for the belt 101 (at least the pouch region 102) is in the illustrated embodiment also selected for some degree of air permeability, thereby allowing for the escape of aroma therapy therefrom to the environs surrounding the subject.

Figure 2C:
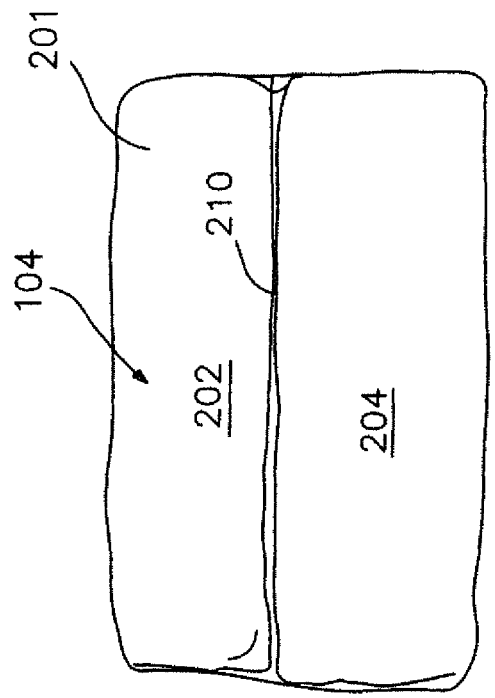
FIGS. 2a-2c are front, side and top elevational views of a first embodiment of a removable therapy pouch useful with the apparatus of FIG. 1.
Figure 2A:
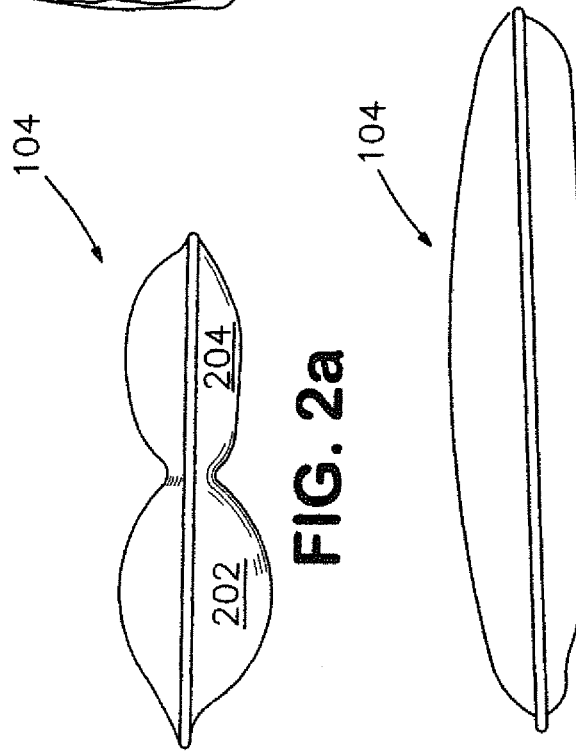
Figure 2B:
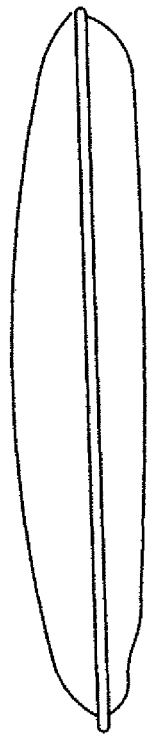
Figure 3:
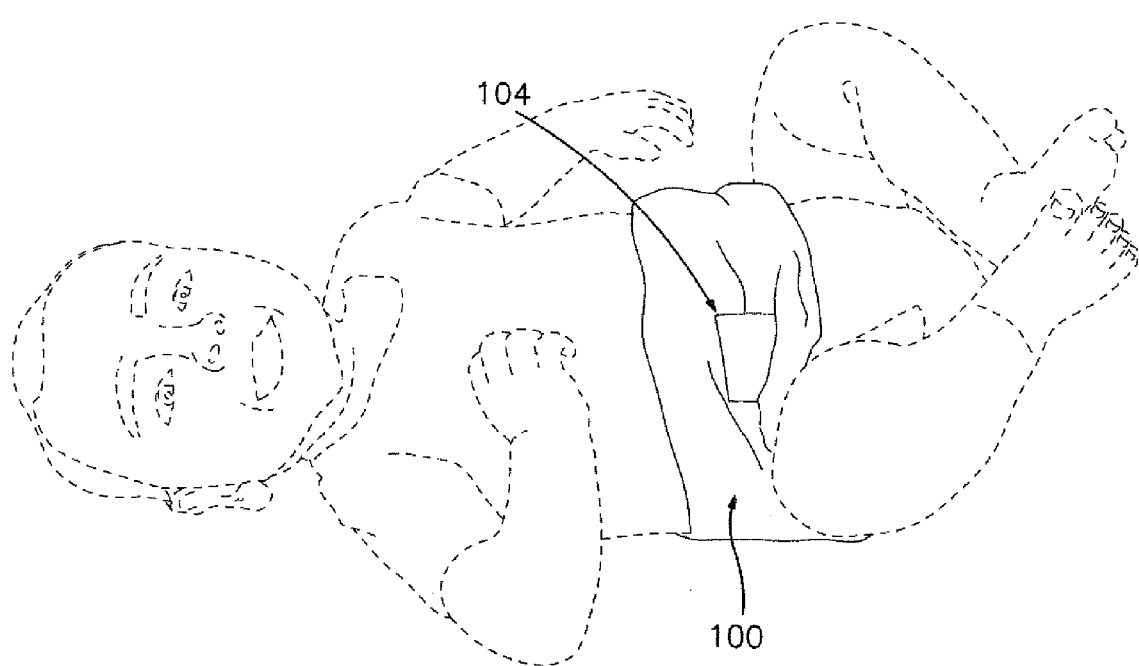
FIG. 3 is a perspective view of a human infant with the apparatus of FIG. 1 applied thereto.

FIGS. 2a-2c illustrate one exemplary embodiment of the removable therapy element 104. The element comprises a generally pouch-like object having a cover comprised of a permeable material such as cotton (open-weave). The longitudinal pockets 202, 204 are formed in the cover 201 by simply stitching the cover sheets together in one or more seams 210, thereby creating cavities into which the medium is disposed. This arrangement allows the medium to be retained at a given position within the element 104 which helps avoid "bunching" of the medium within localized regions of the element 104. As used herein, the term "stitching" refers generally to any process which bonds the cover elements together in a desired location. In the illustrated embodiment, a cotton fabric cover is used, which is sewn together (i.e., using a substantially continuous thread) as is well known in the apparel arts. However, other types of bonding may be used, including for example use of thermally activated adhesives or polymers (akin to "iron-on" hems), standard glues or other adhesives, melting/fusion of polymers or other materials together, mechanical fasteners (ideally non-metallic), and the like.

Furthermore, it will be appreciated that the pockets 202, 204 may be formed in a user-accessible fashion; e.g., by using Velcro or similar material to form removable seams, use of zippers, etc. The sewn variant of the illustrated embodiment, however, has the benefit of mechanical robustness, simplicity, use of only organic materials, and very low cost.

Use of a permeable fabric interface advantageously permits two-way air flow, and escape of the aroma therapy. Furthermore, the permeable interface allows any moisture in the therapy medium in the volume of each pocket 202, 204 to be dissipated, thereby frustrating mold or fungal growth therein. To this end, the interior (and other) surfaces of the cover element 201 can be treated with an anti-mold or anti-fungal agent of the type well known in the art, if desired, in order to further inhibit such formations. In terms of heat transfer, the cover 201 is advantageously configured to permit significant and largely unimpeded heat transfer from the therapy medium to the exterior of the cover 201 (and hence the subject).

Heat can be generated within the medium through any number of processes including conduction, convection, or radiation; however the preferred method of heating for the illustrated embodiment is the conventional magnetron-equipped microwave oven. As is well known in the radio frequency arts, the wavelength of the RF energy emitted by the magnetron is tuned to excite sympathetic molecular vibrations within the medium being heated, thereby inducing rapid (localized) heating within a short period of time. The wavelength of the average microwave (corresponding roughly to 2.4 GHz frequency by $c=\lambda f$) is tuned to excite water molecules ($H_2O$). After a few minutes of heating (depending on size and desired temperature), the therapy element 104 is elevated to the desired thermal energy content, and may be applied to the user. The therapy element can also be heated in situ within the belt 100 if desired for ease of use and handling (rather than separate heating and subsequent insertion).

In one embodiment, the therapy element comprises a substantially "breathable" or permeable material pouch (such as cotton or flannel, although other materials may be used) in which a plurality of therapy components are disclosed. In one variant, these components comprise all-natural components including: (i) berries hard red spring wheat; (ii) flax seed; (iii) peppermint; (iv) spearmint; (v) yarrow flower; (vi) lavender; (viii) chamomile; and (viii) lemon grass.

Specifically, it has been found that the following exemplary proportions are optimal for providing colic or fussiness relief to human infants:

Red berry wheat—4.6 oz.
Herbs: 0.4 oz. to include:
  (i) Lavender
  (ii) Chamomile
  (iii) Peppermint
  (iv) Spearmint
  (v) Yarrow flower
  (vi) Lemon grass
  (vii) flax seed In the exemplary embodiment, the proportions of the 0.4 oz portion (i.e., items (i)-(vii)) are roughly equivalent to one another (i.e., equal). It will be recognized, however, that other proportions and in fact other mixtures of components including some or none of the foregoing, may be used consistent with the invention. However, the inventor hereof has found through testing that the aforementioned mixture and proportions provides a very desirable effect.

Advantageously, the exemplary apparatus is practical and easy to use, requiring no expensive of space-consuming mechanisms, electronics, or the like. It can be used while performing many normal functions such as lying in bed, and even during ambulation (e.g., crawling). It is adapted to maintain its position on the anatomy without slippage, thereby further enhancing its utility and reducing user frustration at having to reposition the apparatus after movement.

Features of the exemplary apparatus of FIGS. 1-2c include, inter alia: (i) safe, immediate, and prolonged heat for the affected area; (ii) Herbal blend provides aromatherapy benefits; (iii) Non-oral application; (iv) durable delivery system; (v) ease and comfort in administration; (vi) can be used both daytime and night time without risk; (vii) retains heat for extended periods and can be easily reheated; (viii) no cords, batteries, or bulky external power; (ix) completely portable and compact; (x) washable fabric cover which is separable from therapy element; (xi) ability to substitute or use additional therapy elements for "tuned" therapy; (xii) use of decorative features and coloration (e.g., stars, animals, cartoon characters, etc.) that are appealing to an infant, and can cause emotional attachment thereto, thereby having the infant view the use of the apparatus on them as a positive experience; (xiii) slim profile and low weight, thereby avoiding interference with sleep, ambulation, mobility, etc.

In other embodiment, as previously referenced, an internal heat source may be used consistent with the apparatus, such as for example: (i) whole grain rice, which when heated can emit "moist heat", and then later recapture at least some moisture during cooldown; (ii) a gel pack or other substantially pliable substance that can be heated in another medium (e.g., boiling water) or heated via microwave energy, (iii) chemically active (exothermic) "instant" heat packs which, for example, generate heat when two or more reactants are brought into contact with one another. Other approaches may be used as well. By affording an internal heat source that is proximate to the therapy components described above, the effect of the latter is intensified, since greater amounts of aroma or other therapy molecules are freed from these components or made airborne under heating. This is especially true in the presence of moist heat, such as may be provided by the aforementioned whole grain rice. The heat itself may also provide soothing for the infant.

Methods

In another aspect of the invention, a method of applying therapy is disclosed. In one embodiment, the method comprises apyrogenic enhancement of body heat production by application of a material (e.g., flannel) belt or waist band containing whole herbs and seeds of rubefacient varieties selected from the Cruciferae class of botanical herbs heated and applied to the abdomen or skin surface, whereby a balance of body heat enhancement and dissipation of heat keeps the body warming effect at a substantially steady level.

In a second embodiment, the method comprises apyrogenic enhancement of body heat production by application of a material belt or waist band containing whole herbs and seeds of rubefacient varieties selected from the Cruciferae class of botanical herbs heated and applied to the abdomen or skin surface, whereby an aromatic discharge of fragrant herbal smells relax and calm the user.

In yet another embodiment, the method comprises apyrogenic enhancement of body heat production by application of a material belt or waist band containing a compartment or pouch for insertion of an internal auxiliary heat source which when applied to the abdominal skin surface, a balance of body heat enhancement and dissipation of heat keeps the body warming effect at a steady level.

It will be appreciated that the use of the apparatus herein also provides opportunity for business methodologies. For example, in one embodiment, the therapy elements 104 are specifically configured to be both replaceable and have a finite lifetime or effectiveness, thereby requiring periodic replacement by the user, akin generally to replaceable razor blade cartridges within a razor handle. These elements can, however, also be configured through design, selection of ingredients, etc. to address specific problems or concerns. For example, the herb mix proportions or constituency may change from element to element, as might its colors, shape, appearance, intended uses, and so forth. Moreover, the longevity of the element may be increased or decreased such as by increasing or decreasing its size, the permeability of the fabric or other covering, the heat which it can sustain (i.e., activation temperature for one or more components), etc. Much as with the aforementioned razor paradigm, the source of profit will generally be in the sales or the replaceable therapy elements, and not the belt 101 itself.

It will be recognized that while certain aspects of the invention are described in terms of a specific sequence of steps of a method, these descriptions are only illustrative of the broader methods of the invention, and may be modified as required by the particular application. Certain steps may be rendered unnecessary or optional under certain circumstances. Additionally, certain steps or functionality may be added to the disclosed embodiments, or the order of performance of two or more steps permuted. All such variations are considered to be encompassed within the invention disclosed and claimed herein.

While the above detailed description has shown, described, and pointed out novel features of the invention as applied to various embodiments, it will be understood that various omissions, substitutions, and changes in the form and details of the device or process illustrated may be made by those skilled in the art without departing from the invention. The foregoing description is of the best mode presently contemplated of carrying out the invention. This description is in no way meant to be limiting, but rather should be taken as illustrative of the general principles of the invention. The scope of the invention should be determined with reference to the claims.

What is claimed:

1. Apparatus for a treatment of colic in a living subject, comprising:
   at least a first portion and a second portion, said first and second portions configured to detachably adjoin to one another;
   wherein said first portion comprises an internal heat source and natural components, said internal heat source comprising red spring wheat berries;
   wherein said second portion comprises an adjustable fastening mechanism and a substantially permeable material configured to permit two-way air flow; and
   wherein said red spring wheat berries have sufficient thermal mass as a whole such that said red spring wheat berries heat said living subject to effect said treatment of said colic.

2. The apparatus of claim 1, wherein said adjustable fastening mechanism of said second portion is configured to adjustably fasten around an abdomen of said living subject.

3. The apparatus of claim 1, wherein said natural components comprise herbs selected for aromatherapeutic effects, and said two-way air flow of said substantially permeable material enables escape of aroma.

4. The apparatus of claim 1, wherein at least said second portion comprises a washable fabric material.

5. The apparatus of claim 1, wherein said permeable material comprises cotton and/or flannel.

6. The apparatus of claim 1, wherein said second portion further comprises another apparatus into which at least a section of said first portion comprising said internal heat source may be inserted.

7. The apparatus of claim 1, wherein application of heat to said natural components via said internal heat source and said two-way air flow of said substantially permeable material enables said living subject to be exposed to a discharge of fragrant herbal aromas, said discharge being configured to mitigate said colic.

8. The apparatus of claim 1, wherein said natural components are selected to be free of neonatal irritants.

9. The apparatus of claim 8, wherein said neonatal irritants comprise one or more of: (i) cinnamon and/or (ii) rosemary.

10. An apparatus for a treatment of colic afflicting an infant, comprising:
    a belt structure configured to wrap around a midsection of an infant, said belt structure comprising a washable material, a fastening apparatus configured to facilitate said belt structure to wrap around said midsection of said infant, and a compartment; and
    a therapy element configured to fit within and be removably adjoined to said compartment of said belt structure, said therapy element comprising:
    a cover comprising a permeable material; and
    at least two pockets, said at least two pockets comprising 4.6 ounces of red berry wheat and an herbal blend;
    wherein said herbal blend is free from neonatal irritants, said neonatal irritants comprising cinnamon and rosemary;
    wherein said therapy element is configured to be heated and emit heat and moisture and recapture said heat and moisture upon cooldown and be disposed and retained proximate to a front central abdomen portion of said infant; and
    wherein said herbal blend comprises 0.4 ounces each of lavender, chamomile, peppermint, spearmint, yarrow flower, lemon grass, and flax seed.

11. The apparatus of claim 10, wherein said permeable material comprises cotton and/or flannel.

* * * * *